United States Patent
Shenk et al.

(10) Patent No.: US 6,560,546 B1
(45) Date of Patent: May 6, 2003

(54) REMOTE ANALYSIS SYSTEM

(75) Inventors: John S. Shenk, Port Matilda, PA (US); Mark O. Westerhaus, State College, PA (US)

(73) Assignee: Infrasoft LLC, Port Matilda, PA (US)

( * ) Notice: Subject to any disclaimer, the term of this patent is extended or adjusted under 35 U.S.C. 154(b) by 228 days.

(21) Appl. No.: 09/633,891

(22) Filed: Aug. 7, 2000

(51) Int. Cl.⁷ .............................................. G01N 37/00
(52) U.S. Cl. ......................... 702/30; 702/27; 702/28; 702/32; 702/188; 356/302; 356/303
(58) Field of Search ......................... 702/30, 23, 50, 702/22, 19, 27, 28, 31, 32, 76–78, 100, 122, 183, 188, FOR 113, FOR 119, FOR 131, FOR 134, FOR 170, FOR 171, FOR 173; 700/266; 356/300, 302, 303, 308, 314, 328, 70, 72, 73; 600/300; 250/252.1 A, 339.01, 339.07–339.09, 339.12, 339.13; 340/631; 422/68.1, 82.05, 82.09; 436/60; 73/53.05

(56) References Cited

U.S. PATENT DOCUMENTS

| | | | |
|---|---|---|---|
| 4,866,644 A | 9/1989 | Shenk et al. ................. 356/319 |
| 4,969,739 A | 11/1990 | McGee ........................ 356/308 |
| 5,489,980 A | 2/1996 | Anthony ..................... 356/308 |
| 5,517,427 A | 5/1996 | Joyce .......................... 702/50 |
| 5,710,713 A | * | 1/1998 | Wright et al. ................ 250/282 |
| 5,717,209 A | | 2/1998 | Bigman et al. ........ 250/339.12 |
| 5,790,977 A | * | 8/1998 | Ezekiel ....................... 702/122 |
| 5,798,526 A | | 8/1998 | Shenk et al. ........... 250/339.09 |
| 5,822,219 A | * | 10/1998 | Chen et al. .................. 356/303 |
| 6,022,315 A | | 2/2000 | Iliff ............................. 600/300 |
| 6,024,699 A | | 2/2000 | Surwit et al. ............... 600/300 |
| 6,049,762 A | * | 4/2000 | Ganz et al. .................. 356/319 |
| 6,138,082 A | * | 10/2000 | Wang et al. ................. 356/319 |
| 6,411,678 B1 | * | 6/2002 | Tomlinson, Jr. et al. ... 379/1.01 |

* cited by examiner

Primary Examiner—Hal Wachsman
(74) Attorney, Agent, or Firm—Richard L. Aitken; Venable

(57) ABSTRACT

Spectrographic instruments at remote site locations measure near infrared absorbance spectra for unknown materials and transmit the absorbance spectra to a central web site where, the measurements are standardized to be the same as if they were measured by a master instrument. The standardized absorbance spectra are then compared with a library of spectra stored at the central web site to select a subset of absorbance spectra from the library which most closely correlate with the absorbance spectrum received from the remote sites. The library spectra are obtained from measurements on materials, the measurable characteristics of which are known. From the selected subset, equations are developed relating the measurable characteristics of the unknown material to the absorbance spectra and from these equations, the measurable characteristics of the unknown materials are determined. The results of this analysis are then transmitted back to the remote site locations electronically.

22 Claims, 3 Drawing Sheets

REMOTE ANALYSIS SYSTEM

This invention relates to near infrared spectrographic analysis, and more particularly to an improved system and method of spectroanalysis wherein reflection or transmission of samples are measured at remote sites and are transmitted to a central location for analysis.

BACKGROUND OF THE INVENTION

Near infrared (NIR) spectrographic instruments are used to provide accurate analysis of materials such as to determine measurable characteristics of the materials. For example, concentrations of constituents of the materials or alternatively physical characteristics of the materials may be measured. In agriculture near infrared spectrographic instruments are used to determine the oil, protein, and moisture content of grain, the fat content of meat, the fat, protein and lactose content of milk, and urea content of milk. In addition, the instruments are used to analyze blood samples, pharmaceutical and synthetic resins.

In typical systems of the prior art, a measurable characteristic is expected to correlate with absorbance at selected wavelengths in the near infrared spectrum. The measurable characteristics of a material can be represented in an equation summing products of weighting coefficients and values from the absorbance spectrum of the material or by an equation summing products of weighting coefficients and values from a derivative of the absorbance spectrum. Typically, a first order derivative of the absorbance spectrum is used, but higher order derivatives may also be used. Collectively, the undifferentiated absorbance spectra and the derivatives of the absorbance spectra are all called absorbance spectra. To measure the concentrations of constituents of an unknown sample or measure physical characteristics of the unknown sample, the absorbances of a multiplicity of known sample materials similar to the unknown material are measured by the spectrographic instrument. The concentrations or the characteristics to be measured in the known sample materials are known. From the absorbance measurements made on the multiplicity of known sample materials, the weighting coefficients of the equations relating the measurable characteristics to the absorbance measurements are determined by multiple regression, by partial least squares of regression or other statistical techniques. The process of determining the values of the weighting coefficients is called calibration. After the coefficients have been determined, the unknown material can be analyzed by the spectrographic instrument using the coefficients that have been determined from the known sample materials. Typically in modern instruments instead of measuring the absorbances at selected specific wavelengths which are known or presumed to correlate with the measurable characteristics, the absorbances of the sample are measured at wavelengths distributed throughout the near infrared spectrum and coefficients and equations relating the measurable characteristics to the absorbance measurements throughout the spectrum are developed by partial least squares, or other statistical technique. The measurable characteristics of the unknown material are then determined by the spectrographic instrument measuring the absorbances of the unknown material and then calculating the measurable characteristics from the measured absorbance values in accordance with the equations. To perform the analysis, the spectrographic instrument is typically provided with a data processor and special software to carry out the analysis. Spectrographic instruments capable of performing material analysis are expensive and a large part of the cost of a spectroanalysis instrument is in the data processor, provided with the necessary software, required to carry out the spectroanalysis. In addition, using the instruments to make the measurements is a relatively complex process, and users of the instruments have to be specially trained. Also the users of the instruments typically require ongoing support to enable the users to consistently make accurate measurements. Because of the relatively high cost of spectroanalysis instruments, the requirements for users of the instruments to be trained, and the requirement for ongoing support, there is a need to reduce the expense and complexity of NIR spectroanalysis of materials.

SUMMARY OF THE INVENTION

In accordance with the present invention, the cost of spectrographic analysis is greatly reduced by eliminating the need for the costly data processors at each spectrographic instrument. In addition, the measurement process is substantially simplified from the user's point of view and the need for special training and ongoing support is eliminated. In accordance with the invention, each spectrographic instrument is provided with the spectrographic hardware to make reflection and/or transmission measurements on sample materials. Each spectrographic instrument site is provided with a simple data processor to receive the spectrographic measurements, convert them to absorbance measurements, and transmit the absorbance measurements to a central site by means of the Internet. At the central location, the spectral data is analyzed to provide the desired measurements on the sample material from which the spectral data were measured.

In order to accurately analyze the spectral data at the central site location, the spectral data must first be standardized so that the spectral data received from any remote location, each having its own spectrographic instrument, is the same as if the spectra obtained from each sample had been measured by the same spectrographic instrument. For this purpose, the central location stores standardization files, one for each remotely located spectrographic instrument of the system. The standardization file for each instrument is generated by comparing absorbance spectra measured by the remote instrument from a standard sample with the absorbance spectra obtained from the standard sample by a master spectrographic instrument. By means of this standardization file the data in the spectra received from the remote sample can be modified to be the same as if it had been measured by the master instrument.

The central location also stores a library of spectra for a large number of different samples, the composition or other measurable characteristics of which are known. The spectra obtained from the unknown sample is compared with the library spectra to determine by a mathematical process weighting coefficients of functions relating absorbance values to the characteristics being measured. In the preferred embodiment the spectrum from the unknown sample is first compared by correlation with the spectra from the known samples in the library to find a set of spectra which closely correlate with the spectra from the unknown sample. For example, 100 spectra in the library which most closely correlate with the unknown sample may be selected. The selected spectra from the library are then used to generate a set of weighting coefficients for the unknown sample. Alternatively the unknown spectrum can be compared with the entire library of spectra using neural networks to determine the weighting coefficients of neural network functions. The coefficients are multiplied times the absorbance values in the spectrum from the unknown sample to provide an analysis of the sample.

The analysis of the unknown sample may then be transmitted electronically to the user at the remote site. The spectra of the unknown sample may be added to the library of spectra at the central site along with the characteristics of the unknown material determined by conventional laboratory methods.

By having the analysis performed at a central site, the need for training personnel to use the instrument, the ongoing support of such personal, and the need for a costly computer at each remote site are eliminated. In addition, advantageous use may be made of a large library of spectra at the central site without having to duplicate this library at each remote location. As a result, spectroanalysis is substantially greatly simplified for users and its cost is substantially reduced.

DETAILED DESCRIPTION OF A PREFERRED EMBODIMENT

Figure 1:
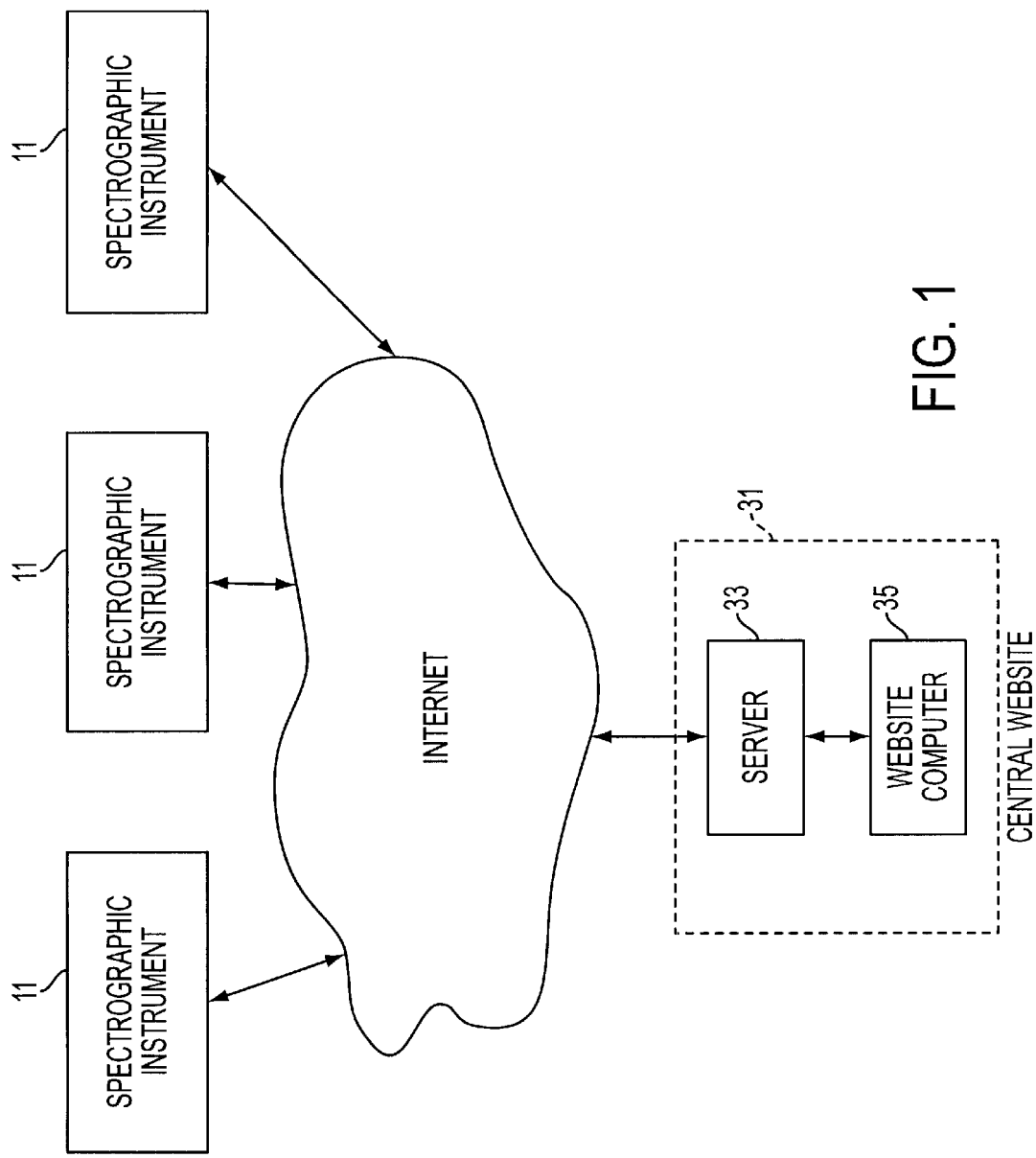
FIG. 1 is a block diagram of the system of the invention.
Figure 2:
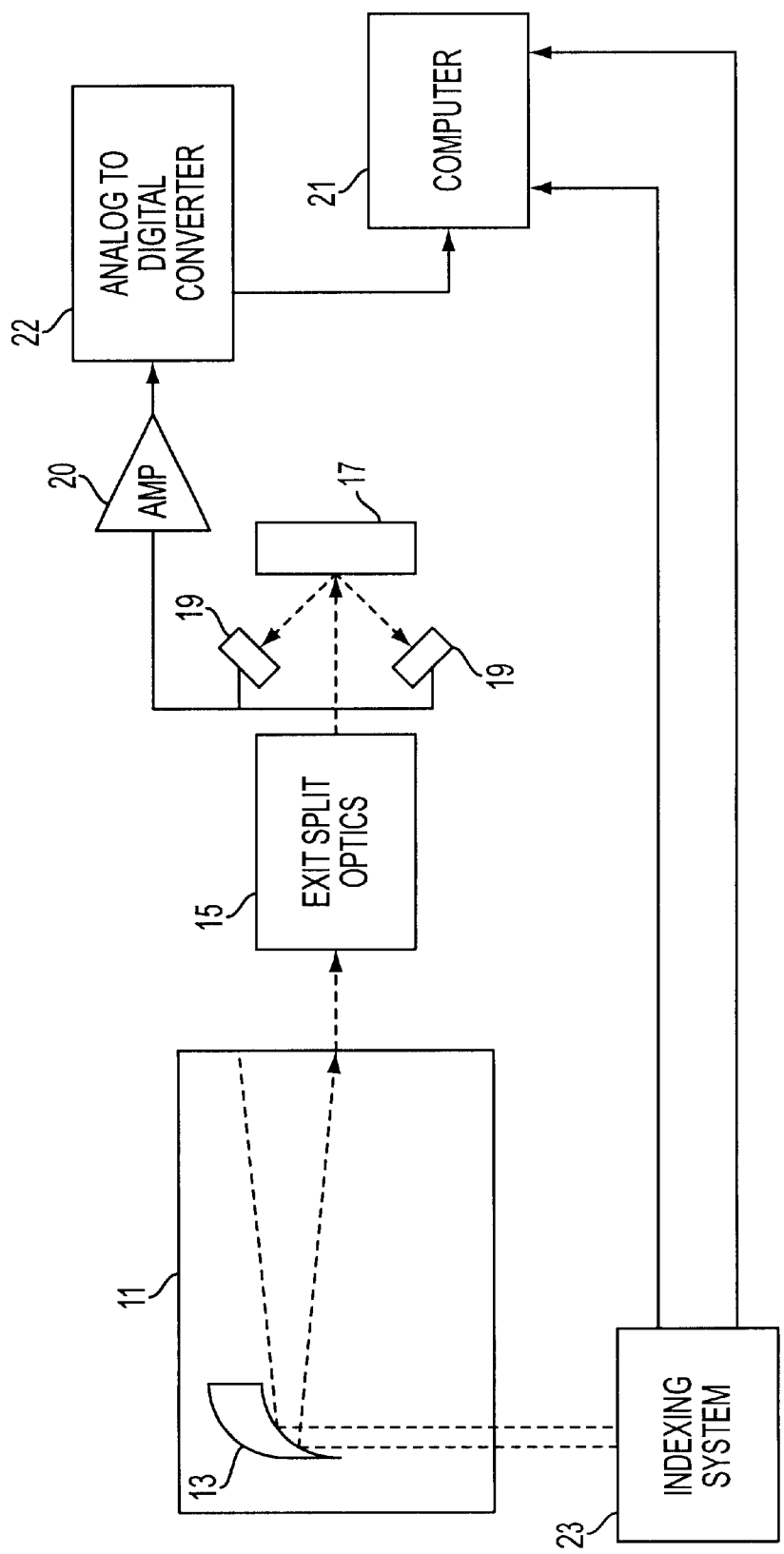
FIG. 2 is a schematic illustration of a spectrographic instrument of the type used in the preferred embodiment of the invention.
Figure 3:
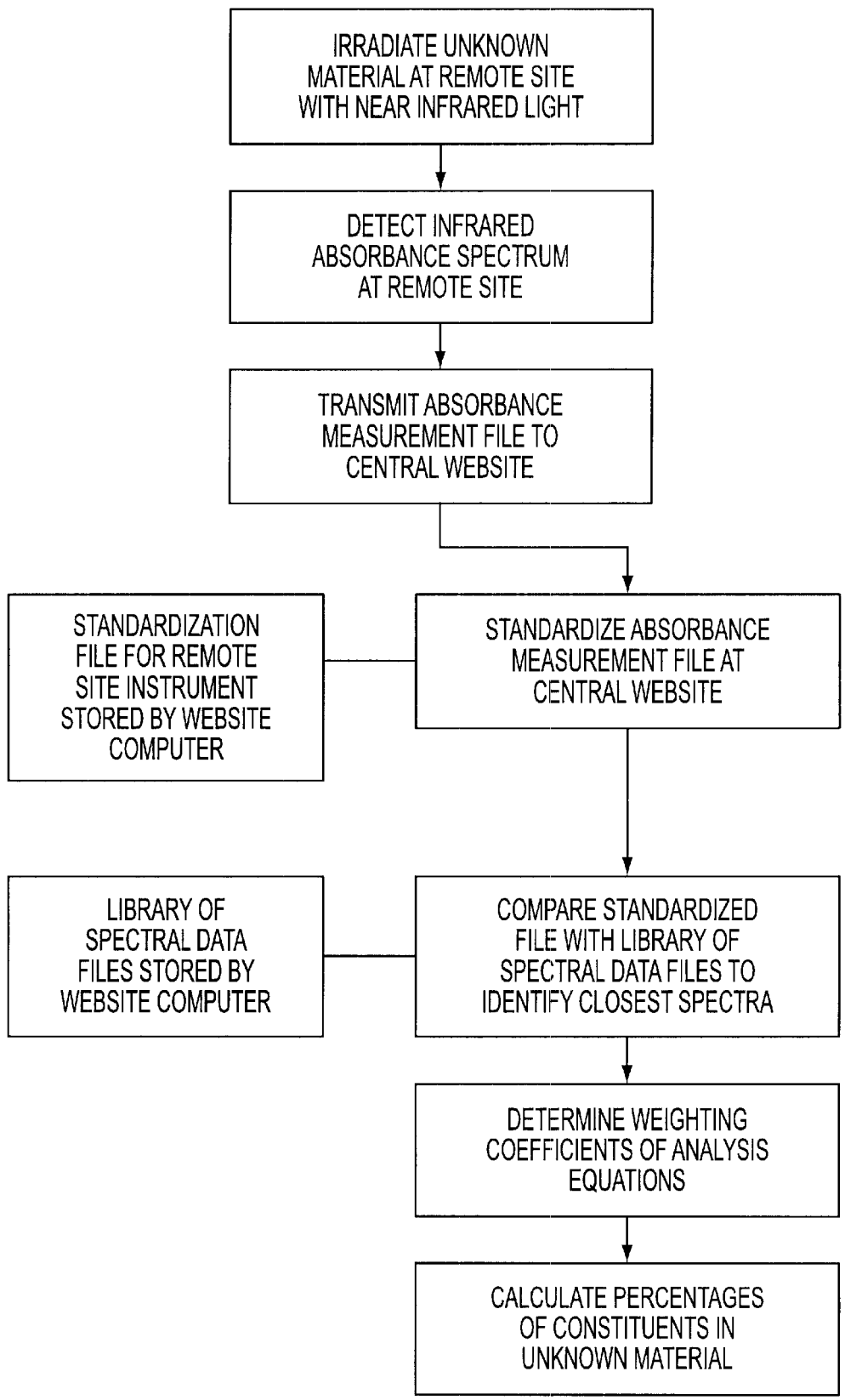
FIG. 3 is a flow chart illustrating the method of the invention.

As shown in FIG. 1, near infrared spectrographic instruments 11 are provided at widely separated remote sites which can be found anywhere in the world having access to the Internet. The hardware of each spectrographic instrument to make the measurements on a sample of material may be similar to that disclosed in U.S. Pat. No. 4,969,739. Each spectrographic instrument is capable of measuring the intensity of NIR light reflected from or transmitted through a sample at narrow wavelength bands distributed throughout the near infrared spectrum. As shown in FIG. 2, each spectrographic instrument is provided with an oscillating grating 13 which is illuminated by broadband near infrared light. The grating 13 disburses the light into a near infrared spectrum and a narrow bandwidth (for example a bandwidth of about ten nanometers) of the spectrum will be transmitted through exit slit optics 15 to a sample 17. As the grating oscillates, the center wavelength of the wavelength of the light that irradiates the sample is swept through the near infrared spectrum. Light diffusely reflected by the sample is detected by near infrared photodetectors 19. The output from the photodetectors is amplified by an amplifier 20 and processed by a simple data processor 21. An indexing system 23 generates pulses as the grating 13 oscillates and applies these pulses to the data processor 21. In response to the pulses from the indexing system 23, the computer converts successive samples from the output signal of the amplifier 20 to digital values. Each digital value thus will correspond to the diffuse reflection intensity of the sample at a specific wavelength in the near infrared range. The computer 21 monitors the angular position of the grating 13 as indicated by the pulses from the indexing system 23 and, accordingly, monitors the wavelength irradiating the sample as the grating oscillates. The pulses produced by the indexing system define incremental index points at which values of the output signal of the amplifier converted to digital values to thus obtain a digital representation of the reflected intensity from the sample throughout the spectrum. In the case of a highly transmissive sample, one or more photodetectors will be positioned to detect the intensity of the light transmitted through the sample. The data processor at the remote instrument will convert the intensity measurements into measurements representing the absorbance of the material. Typically, this conversion involves dividing the intensity measurements by values representing the intensity with which the sample is irradiated to determine reflectance values or transmittance values and then calculating the logarithm of the inverse of the reflectance or transmittance values.

At the time the measurements are made, the operator will enter a product code and a sample number. The product code identifies the material of the sample and the sample number identifies a particular sample being measured. When the absorbance spectrum has been measured and the product code and the sample number have been entered, an Internet access program residing on the data processor at the remote site will transmit an analysis order via the Internet or other network to a central web site location 31, shown in FIG. 1. The analysis order will contain an identification of the remote site, the product code, sample number and an instrument registration number uniquely identifying the spectrographic instrument which measured the absorbance spectrum of the sample. This data will be transmitted with an absorbance measurement file containing the absorbance spectrum measured by the spectrographic instrument at the remote site. At the central web site location 31, the web site server 33 receives the analysis order and temporarily stores it. The server 33 is connected with a web site computer 35 which continuously monitors the server for analysis orders. When the web site computer 35 finds an order, it downloads the corresponding absorbance measurement file into its input directory and signals the server to erase the downloaded analysis order including the absorbance measurement file. The absorbance measurement file in the input subdirectory is then standardized in accordance with the method described in U.S. Pat. No. 4,866,644, which issued Sep. 12, 1989 to John S. Shenk and Mark O. Westerhaus. This patent is hereby incorporated by reference. In accordance with the standardization technique described in the Schenk et al patent, the values in the absorbance measurement file obtained from an unknown sample by the remote instrument are modified to be the same as if they were measured by a particular master instrument. The standardization process makes use of a standardization file for the remote instrument, which standardization file is stored in the web site computer. As disclosed in the Schenk et al. patent, the index points at which measurements are made by the remote instrument will not be at precisely the same wavelengths as the index points on which measurements would be made by the master instrument. The standardization process determines the wave shift between each index point of the remote instrument and the corresponding index point on the master instrument to locate the master instrument index points relative to the remote instrument index points. The location of the index points of the master instrument relative to the index points of the remote site instrument forms part of the standardization file for the remote site instrument. This portion of the standardization file is used in a first step of the standardization process to determine the spectrum measurements of the remote site instrument at the index points of the master instrument. The index points of the master instrument will fall between the index points of the remote site instrument and the spectrum measurements of the remote site instrument are determined from the actual measurements of the remote site instrument by interpolation. The absorbance values at these index points need to be adjusted for photometrics wherein each value is corrected with an addition factor and a multiplication factor. The addition factors and the multiplication factors are uniquely determined for each index point of the master as located on the remote site instrument and form part of the standardization file for the remote site instrument. The addition and multiplication factors are determined in the process of generating the standardization file for the remote site instrument by comparing the interpolation corrected measurements of absorbance spectra by the remote site instrument on test samples with measurements of absorbance spectra made by the master instrument on the test samples. To standardize an absorbance measurement file received at the central web site from a remote site instrument, the web site computer 35 locates the standardization file for the remote site instrument for the remote site instrument from the remote instrument registration number and corrects the absorbance measurements in the absorbance measurement file in accordance with the standardization file. This process involves first correcting the spectrum measurements by interpolation in accordance with the master instrument index points located on the remote site instrument and then adjusting these corrected values by the corresponding addition and multiplication factors in the standardization file as described in the above-identified Shenk et al. patent. The data may be further processed by taking the first or second derivative of the data.

Following these operations in the preferred embodiment, the absorbance spectrum from the unknown sample, called the target spectrum, is compared with a library of absorbance spectra stored by the web site computer to identify the closest 100 absorbance spectra. This process is carried out in the manner described in U.S. Pat. No. 5,798,526, issued Aug. 25, 1998, John S. Shenk and Mark O. Westerhaus. U.S. Pat. No. 5,798,526 is hereby incorporated by reference. As described in Pat. No. 5,798,526, the closest 100 absorbance spectra are identified by correlating a compressed version of the target absorbance spectrum with the library spectra which have been compressed in a similar manner. The 100 library spectra which have the highest correlations with the target spectrum are selected to be used to compute the weighting coefficients to carry out the analysis of the unknown material. Alternatively, instead of using the methods described in U.S. Pat. No. 5,798,526 to select the closest spectra, the method described in U.S. Pat. No. 5,822,219, issued Oct. 13, 1998, to Xiaolin Chen and Stephen L. Monfre may be used to select from the library the spectra which most closely match the unknown material. After the spectra from the library have been selected, the Mahalanobis distance between the vector of PLS scores for the absorbance values of the spectrum obtained from the unknown sample and the mean of the vectors represented by the selected 100 spectra from the library is determined. In addition, the distance between the vector of the spectrum of the unknown sample and each vector of the 100 spectra selected from the library is also calculated in the same manner as calculating a Mahalanobis distance. If the Mahalanobis distance to the selected subset of vectors and the distance to the nearest vector of the library subset are not within selected tolerance limits, the unknown sample is determined to be insufficiently similar to the spectra in the library to do an accurate analysis of the unknown material. Under these circumstances, the web site computer sends electronically a message back to the data processor at the remote station at which the unknown sample was measured indicating that the unknown sample cannot be analyzed accurately.

If the Mahalanobis distance between the PLS scores of the target spectrum for the unknown sample and the mean of the 100 selected library spectra and the distance between the vector of the unknown sample and the nearest vector of the library spectra are both within the tolerance limits, the web site computer then proceeds into a partial least squares routine to begin the analysis of the material. As a first step of this process, the system determines the weighting coefficients of the analysis equations from the selected 100 samples by partial least squares regression. More specifically, assuming the characteristics being measured are the concentrations of the constituents of the unknown sample, the equations for determining the concentrations of the constituents being measured in a material are represented as follows:

$$C_1 = K_{11}A_1 + K_{12}A_2 + K_{13}A_3 + \cdots K_{1n}A_n$$

$$C_2 = K_{21}A_1 + K_{22}A_2 + \cdots K_{2n}A_n$$

$$C_3 = K_{31}A_1 + K_{32}A_2 + \cdots K_{3n}A_n$$

$$\vdots$$

$$C_m = K_{mi}A_1 + K_{m2}A_2 + \cdots K_{mn}A_n$$

In the equation, $C_1$ through $C_m$ are the concentrations of the constituents being measured, $A_1$ through $A_n$ are the values of the absorbance spectrum from the unknown material, and $K_{11}$ through $K_{mn}$ are the weighting coefficients to be determined by the partial least squares. For the 100 known samples corresponding to the selected subset of spectra, the concentrations $C_1$ through $C_m$ are known and the absorbance values $A_1$ through $A_n$ are known, being provided in the corresponding library spectra. From these known values, the weighted coefficients $K_{11}$, through $K_{mn}$ are determined by partial least squares. The equations with the coefficients determined in this manner are then used to calculate the percentage of each constituent from the corresponding equation in the manner described in U.S. Pat. No. 5,798,526. This analysis is transmitted electronically to the remote location at which the unknown material was measured.

If one or more physical properties of the unknown material are to be measured, the spectra in the library should include spectra from samples which are similar to the analysis material being analyzed and for which the quantified physical properties are known. From these library spectra, the 100 which have the closest correlation to the target spectrum are selected. From the selected 100 spectra, the coefficients of equations relating the physical properties to the spectral values in the selected library spectra are determined in the same manner as described above for determining the constituent percentages of the analysis sample.

If the absorbance spectrum of the unknown sample is not well represented in the library of spectra, the absorbance spectrum of the unknown sample is added to the library as a known material along with its characteristics as determined by traditional laboratory methods so that the new absorbance spectrum can be used in future analyses of material.

In the system described above, only one central web site is disclosed. It is contemplated in addition to this central web site additional satellite web sites will also be provided wherein each satellite web site will perform analyses for other remote site locations in the same manner that the web site 31 provides analyses of materials measured by the remote site instruments 11.

In the system as described above, the remote site instruments measure only the absorbance spectrum of the unknown material and transmits this data to the central web site. All of the processing of the data including smoothing, differentiating, standardization is all carried out at the web site 31. However, it should be understood that some or all of the above-described data processing could be carried out at the remote web site.

As described above, the coefficients of functions relating the measurable quantities to the absorbance values are determined by partial least squares. Instead of determining these coefficients by partial least squares, these coefficients could be determined by other statistical techniques, such as multiple regression and neural networks.

As described above, the system of the invention analyzes an unknown material from its absorbance spectrum. Absorbance measurements are used because they generally are proportional to concentrations of constituents or other properties of the material to be measured. It will be apparent that the system is applicable to representations of the reflectance or transmittance measurements in other forms. In the preferred embodiment as described above, the spectrographic measurements are made in the near infrared range, which is typically described as extending from 780 to 2500 nanometers. The system of the invention can also be used outside of this range such as for example from 500 to 5000 nanometers.

As described above the preferred embodiment of the invention uses a grating to disperse the light into a spectrum. The system as described can also be applied to measurements collected by FT-IR instruments, filter instruments, diode array instruments, prism instruments, or any type of instrument enabling absorption measurements to be made at narrow band wavelengths.

These and many other modifications may be made to the above-described specific embodiments of the invention without departing from the spirit and scope of the invention, which is defined in the appended claims.

What is claimed is:

1. A system for analyzing materials comprising:
  a plurality of remote spectrographic instruments at different remote locations, said remote spectrographic instruments being operable to measure reflected intensities of diffusely reflected light from analysis samples of material to be analyzed at narrow wavelength bandwidths distributed throughout a spectral range, and
  data processing equipment comprising
    a remote data processor at each remote location and
    a central data processor at a central web site,
  said remote data processors being programmed to transmit spectral data files corresponding to the reflected intensity measurements to said central web site, said data processing equipment being programmed to produce standardized data files in which reflected intensity measurements made by said remote spectrographic instruments are adjusted to be the same as if they were made by the same master spectrographic instrument, said central data processor storing a library of spectral data files corresponding to reflected intensity measurements made by said master spectrographic instrument on known materials, said central data processor being programmed to compare said standardized data files with the spectral data files of said library to determine by a mathematical process sets of coefficients for functions relating measurable characteristics of the materials of analysis samples to the data in corresponding standardized data files, to determine from said functions said measurable characteristics of the materials of analysis samples and to transmit said measurable characteristics to the corresponding remote locations.

2. The system for analyzing materials as recited in claim 1, wherein said standardized data files comprise absorbance measurements of materials of analysis samples and wherein said spectral data files of said library comprise absorbance measurements of said known materials.

3. The system for analyzing materials as recited in claim 1, wherein said data processing equipment produces said standardized data files by adjusting said reflected intensity measurements made by said remote spectrographic instruments in accordance with the wave shift between the index points of said remote spectrographic instruments and said master spectrographic instrument and for the difference in the photometrics between said master spectrographic instrument and said remote spectrographic instruments.

4. The system for analyzing material as recited in claim 1, wherein said central data processor stores standardization files each corresponding to a remote spectrographic instrument, and wherein said central data processor is programmed to produce said standardized data files by adjusting said reflected intensity measurements made by said remote spectrographic instruments in accordance with the corresponding standardization files.

5. A system for analyzing materials comprising a plurality of remote spectrographic instruments at different remote locations, said remote spectrographic instruments being operable to measure reflected intensities of diffusely reflected light from analysis samples of material to be analyzed at narrow wavelength bandwidths distributed throughout a spectral range, and
  data processing equipment comprising
    a remote data processor at each remote location and
    a central data processor at a central web site,
  said remote data processors being programmed to transmit spectral data files corresponding to the reflected intensity measurements to said central web site, said data processing equipment being programmed to produce standardized data files in which the reflected intensity measurements made by said remote data processors are adjusted to be the same as if they were made by the same master spectrographic instrument, said central data processor storing a library of spectral data files corresponding to reflected intensity measurements made by said master spectrographic instrument on known materials, said central data processor being programmed to compare said standardized data files with the spectral data files of said library to select subsets of the spectral data files of said library wherein the spectral data files of each subset are the most similar to a corresponding standardized data file, said central data processor being programmed to determine from each subset a set of coefficients for an equation relating a measurable characteristic of an analysis sample to the data in the corresponding standardized data file, to determine from said equation said measurable characteristic, and to transmit said measurable characteristic to the corresponding remote location.

6. The system for analyzing materials as recited in claim 5, wherein said central data processor is programmed to determine from each subset a set of coefficients for a plurality of equations relating a plurality of measurable characteristics of an analysis sample to the data in a corresponding standardized data file, said central data processor being further programmed to determine said plurality of measurable characteristics from said plurality of equations.

7. A system for analyzing materials comprising
  a plurality of remote spectrographic instruments at different remote locations, said remote spectrographic instruments being operable to measure transmitted intensities of light transmitted through analysis samples of material to be analyzed at narrow wavelength bandwidths distributed throughout a spectral range, and data processing equipment comprising
a remote data processor at each remote location and a central data processor at a central web site, said remote data processors being programmed to transmit spectral data files corresponding to the transmitted intensity measurements to said central web site, said data processing equipment being programmed to produce standardized data files in which the transmitted intensity measurements made by said remote data processors are adjusted to be the same as if they were made by the same master spectrographic instrument, said central data processor storing a library of spectral data files corresponding to transmitted intensity measurements made by said master spectrographic instrument on known materials, said central data processor being programmed to compare said standardized data files with the spectral data files of said library to determine by a mathematical process sets of coefficients for functions relating measurable characteristics of the materials of analysis samples to the data in corresponding standardized data files, to determine from said functions said measurable characteristics and to transmit said measurable characteristics to the corresponding remote location.

8. The system for analyzing materials as recited in claim 7, wherein said standardized data files comprise absorbance measurements of said analysis samples and wherein said spectral data files of said library comprise absorbance measurements of said known materials.

9. The system for analyzing materials as recited in claim 7, wherein said data processing equipment produces said standardized data files by adjusting the transmitted intensity measurements made by said remote spectrographic instruments in accordance with the wave shift between the index points of said remote spectrographic instruments and said master spectrographic instrument and for the difference in the photometrics between said master spectrographic instrument and said remote spectrographic instruments.

10. The system for analyzing material as recited in claim 7, wherein said central data processor stores standardization files each corresponding to a remote spectrographic instrument, and wherein said central data processor is programmed to produce said standardized data files by adjusting intensity measurements made by said spectrographic instruments in accordance with the corresponding standardization files.

11. A system for analyzing materials comprising
a plurality of remote spectrographic instruments at different remote locations, said remote spectrographic instruments being operable to measure transmitted intensities of light transmitted through analysis samples of material to be analyzed at narrow wavelength bandwidths distributed throughout a spectral range, and data processing equipment comprising
a remote data processor at each remote location and a central data processor at a central web site, said remote data processors being programmed to transmit spectral data files corresponding to the transmitted intensity measurements to said central web site, said data processing equipment being programmed to produce standardized data files in which the transmitted intensity measurements made by said remote data processors are adjusted to be the same as if they were made by the same master spectrographic instrument, said central data processor storing a library of spectral data files corresponding to transmitted intensity measurements made by said master spectrographic instrument on known materials, said central data processor being programmed to compare said standardized data files with the spectral data files of said library to select subsets of the spectral data files of said library wherein the spectral data files of each subset are the most similar to a corresponding standardized data file, said central data processor being programmed to determine from each subset a set of coefficients for an equation relating a measurable characteristic of the material of an analysis sample to the data in the corresponding standardized data file, to determine from said equation said measurable characteristic, and to transmit said measurable characteristic to the corresponding remote location.

12. The system for analyzing materials as recited in claim 11, wherein said central data processor is programmed to determine from each subset a set of coefficients for a plurality of equations relating a plurality of measurable characteristics of an analysis material to the data in a corresponding standardized data file, said central data processor being further programmed to determine said plurality of measurable characteristics from said plurality of equations.

13. A method of analyzing materials comprising
irradiating a material with light, detecting at a remote location with a remote spectrographic instrument the intensity of light diffusely reflected from said material at narrow wavelength bandwidths distributed through a spectrum, transmitting a spectral data file corresponding to the detection of reflected intensities to a central web site, producing a standardized file of data in which the reflected intensities detected by the remote spectrographic instrument are adjusted to be the same as if they were measured by a master spectrographic instrument, storing at said central web site a library of spectral data files, each corresponding to spectrographic reflectance intensity measurements made on a known material by said master spectrographic instrument, comparing said standardized file of data with said library of spectral data files to determine by a mathematical process in a central data processor at said web site the coefficients of a function relating a measurable characteristic of said material to the data in said standardized file of data, determining said measurable characteristic from said function, and transmitting said measurable characteristic to said remote location.

14. The method of analyzing materials as recited in claim 13, wherein said standardized file of data is produced at said central web site from the spectral data file transmitted to said central web site.

15. The method of analyzing a material as recited in claim 14, further comprising storing at said central web site a standardization file for said remote spectrographic instrument corresponding to differences in measurements made by said remote spectrographic instrument and said master spectrographic instrument on a common material, said standardized file of data being produced from the spectral data file transmitted to central web site by adjusting such standardized file of data in accordance with said standardization file.

16. A method of analyzing materials comprising irradiating a material with light, detecting at a remote location with a remote spectrographic instrument the intensity of light diffusely reflected from said material at narrow wavelength bandwidths distributed through a spectrum, transmitting a measurement file of data corresponding to the detected reflected intensities to a central web site, producing a standardized file of data in which the reflected intensities detected by said remote spectrographic instrument are adjusted to be the same as if they were detected by a master spectrographic instrument, storing at said central web site a library of spectral data files, each corresponding to spectrographic reflectance intensity measurements made on a known material by said master spectrographic instrument, comparing said standardized file of data with said library of spectral data files to select a subset of spectral data files which are most similar to said standardized file, determining from said subset, in a central data processor at said web site, the coefficients of an equation relating a measurable characteristic of said material to the data in said standardized file, determining in said central data processor said measurable characteristic from said equation, and transmitting said measurable characteristic to said remote location.

17. A method as recited in claim 16 further comprising determining whether the difference between said standardized file of data and the nearest spectral data file in the selected subset of spectral data files is within a predetermined tolerance.

18. A method of analyzing materials comprising irradiating a material with light, detecting at a remote location with a remote spectrographic instrument the intensity of light transmitted through said material at narrow wavelength bandwidths distributed through a spectrum, transmitting a spectral data file corresponding to the detection of transmitted intensities to a central web site, producing a standardized file of data in which the intensities detected by said remote spectrographic instrument are adjusted to be the same as if they were measured by a master spectrographic instrument, storing at said central web site a library of spectral data files, each corresponding to spectrographic transmitted intensity measurements made on a known material by said master spectrographic instrument, comparing said standardized file of data with said library of spectral data files to determine by a mathematical process in a central data processor at said web site the coefficients of a function relating said measurable characteristic to the data in said standardized file, determining in said central data processor a measurable characteristic of said material from said function, and transmitting said measurable characteristic to said remote location.

19. The method of analyzing materials as recited in claim 18, wherein said standardized file of data is produced at said central web site from the spectral data file transmitted to said central web site.

20. The method of analyzing a material as recited in claim 19, further comprising storing at said central web site a standardization file for said remote spectrographic instrument corresponding to differences in measurements made by said remote spectrographic instrument and said master spectrographic instrument on a common material, said standardized file of data being produced from the spectral data file transmitted to said central web site by adjusting such spectral data file in accordance with said standardization file.

21. A method of analyzing materials comprising irradiating a material with light, detecting at a remote location with a remote spectrographic instrument the intensity of light transmitted through said material at narrow wavelength bandwidths distributed through a spectrum, transmitting a measurement file of data corresponding to the detection of transmitted intensities to a central web site, producing a standardized file of data in which the intensities detected by said remote spectrographic instrument are adjusted to be the same as if they were measured by a master spectrographic instrument, storing at said central web site a library of spectral data files, each corresponding to spectrographic transmitted intensity measurements made on a known material by said master spectrographic instrument, comparing said standardized file of data with said library of spectral data files to select a subset of spectral data files which are most similar to said standardized file of data, determining from said subset, in a central data processor at said web site, the coefficients of an equation relating said measurable characteristic to the data in said standardized file, determining in said central data processor a measurable characteristic of said material from said equation, and transmitting said measurable characteristic to said remote location.

22. A method as recited in claim 21 further comprising determining whether the difference between said standardized file of data and the nearest spectral data file in the selected subset of spectral data files is within a predetermined tolerance.

* * * * *